United States Patent [19]

Hall et al.

[11] 4,115,431
[45] Sep. 19, 1978

[54] SUBSTITUTED DIMETHYL DIHYDROXY BENZENE AND CYCLOHEXADIENE COMPOUNDS AND USES THEREOF FOR AUGMENTING OR ENHANCING THE TASTE AND/OR AROMA OF CONSUMABLE MATERIALS INCLUDING TOBACCOS, PERFUMES AND PERFUMED ARTICLES

[75] Inventors: John B. Hall, Rumson; Mark A. Sprecker, Sea Bright, both of N.J.; Edward J. Shuster, Brooklyn, N.Y.; Frederick Louis Schmitt, Holmdel; Joaquin F. Vinals, Red Bank, both of N.J.

[73] Assignee: International Flavors & Fragrances Inc., New York, N.Y.

[21] Appl. No.: 800,889

[22] Filed: May 26, 1977

[51] Int. Cl.$^2$ .......................................... C07C 121/52
[52] U.S. Cl. ................................. 260/465 F; 260/464; 260/585 R; 131/144; 252/89 R; 252/174; 252/522; 424/69; 424/358
[58] Field of Search ............................ 260/464, 465 F

[56] References Cited

U.S. PATENT DOCUMENTS 4,072,660  2/1978  Muller et al. ............... 260/465 F X

OTHER PUBLICATIONS

Barnes, J.A.C.S., 70, (1948), pp. 145–146.
C.A., 59, (1963), Geigy, 11444b.
Rodd's Chemistry of Carbon Compounds, Coffey-Editor, 2nd ed., vol. III–Part A, (1971), pp. 137–143.

*Primary Examiner*—Joseph Paul Brust
*Attorney, Agent, or Firm*—Arthur L. Liberman; Harold Haidt; Franklin D. Wolffe

[57] ABSTRACT

Processes and compositions are described for the use in tobacco flavor and aroma and perfume aroma augmenting, modifying, enhancing and imparting compositions and as tobacco, perfume and perfumed article aroma imparting and augmenting materials of one or more substituted dimethyl dihydroxy benzene and/or cyclohexadiene compounds, represented either by the equilibrium mixture:

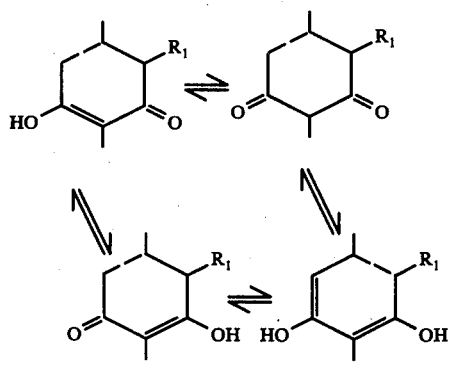

(and other tautomers) or by one of the compounds which is a constituent of said equilibrium mixture, wherein the dashed line represents a carbon-carbon single bond or a carbon-carbon double bond and $R_1$ is either acetyl having the structure:

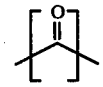

or nitrile having the structure:

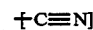

with the proviso that when the dashed line is a carbon-carbon single bond, $R_1$ is only nitrile and when the dashed line is a carbon-carbon double bond, $R_1$ is either nitrile or acetyl.

Also described is the class of novel compounds represented either by the equilibrium mixture:

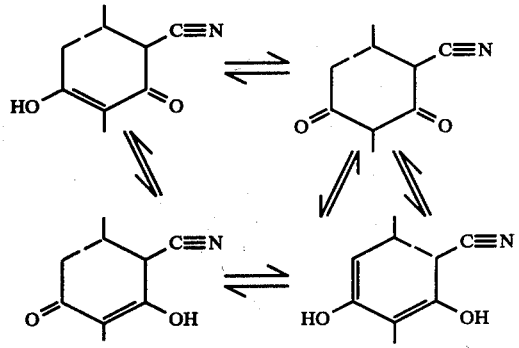

(and other tautomers) or by one of the components of the equilibrium mixture wherein the dashed line is a carbon-carbon single bond or a carbon-carbon double bond.

The above-mentioned compounds, taken alone or in combination, provide and/or enhance and/or enrich "Oak Moss" notes in perfumes such as "Mousse de Chene". These compounds also provide sweet, slightly woody, "Oak Moss"-like aromas in the mainstream and sidestream on smoking and prior to smoking in tobacco articles such as cigarettes and cigars.

1 Claim, 4 Drawing Figures

FIG.2

IR SPECTRUM ACCORDING TO EXAMPLE I

FIG.4 IR SPECTRUM ACCORDING TO EXAMPLE II

SUBSTITUTED DIMETHYL DIHYDROXY BENZENE AND CYCLOHEXADIENE COMPOUNDS AND USES THEREOF FOR AUGMENTING OR ENHANCING THE TASTE AND/OR AROMA OF CONSUMABLE MATERIALS INCLUDING TOBACCOS, PERFUMES AND PERFUMED ARTICLES

BACKGROUND OF THE INVENTION

The present invention relates to substituted dimethyl dihydroxy benzene and cyclohexadiene compounds and mixtures thereof as well as the uses thereof for augmenting or enhancing the taste and/or aroma of perfumes, perfumed articles, tobaccos and/or tobacco flavoring compositions. These substituted dimethyl dihydroxy benzene and cyclohexadiene compounds are represented by the generic structures:

(and other tautomers) wherein the dashed line represents a carbon-carbon single bond or a carbon-carbon double bond and $R_1$ is either acetyl having the structure:

or nitrile having the structure:

with the proviso that when the dashed line is a carbon-carbon single bond, $R_1$ is nitrile. In addition, certain of these compounds are novel compounds; wherein $R_1$ is nitrile and the dashed line is a carbon-carbon single bond or a carbon-carbon double bond There has been considerable work performed relating to substances which can be used to impart (modify, augment or enhance) tobacco flavors and fragrances to (or in) various consumable materials including tobaccos, tobacco articles, perfumes, colognes and perfumed articles, such as soaps, cosmetics, cosmetic powders and detergents. These substances are used to diminish the use of natural materials, some of which may be in short supply and to provide more uniform properties in the finished product.

Sweet, "Oak Moss", woody and smoke-like aromas prior to smoking and, in the mainstream and in the sidestream on smoking are desirable in tobaccos and in tobacco flavoring compositions.

"Oak Moss"-like or "Mousse de Chene" aromas and notes are highly desirable in several types of perfume compositions, perfumed articles and colognes.

Furthermore, in the art of perfumery, the extracts of lichens such as those marketed under the name of "Oak Moss" have become indispensable and are widely used as materials for perfumes. The natural extracts of "Oak Moss", however, have limited availability and are very expensive. Compounds such as 2,4-dihydroxy-3-methyl-benzaldehyde having the chemical structure:

described in U.S. Pat. No. 3,975,309 issued on Aug. 17, 1976 and indicated to be prepared by Jones and Robertson [Journal of the Chemical Society, London, page 1691 (1932)], as well as compounds such as 2,4-dihydroxy-3,6-dimethyl-1-carboalkoxybenzenes and alkyl homologues thereof as described in U.S. Pat. Nos:

3,634,491 — Issued on Jan. 11, 1972
3,701,801 — Issued on Oct. 31, 1972
3,729,430 — Issued on Apr. 24, 1973 and Mexican Pat. No. 126,927, issued on Dec. 16, 1971 (corresponding to published Dutch application No. 7,200,076, filed on Jan. 4, 1972) have been previously found to be useful "Oak Moss" "substitutes". However, complete "Oak Moss" fragrance formulations, to date, have not been achieved in the perfumery industry; nor have such complete "Oak Moss" fragrances been achieved in the tobacco industry for the purposes of flavoring and aromatizing smoking tobacco articles, such as cigarettes and cigars.

Furthermore, nothing in the prior art sets forth the unexpected, advantageous properties of the compounds of the instant invention in their ability to enhance and augment particularly on dry-out "Oak Moss" fragrances, as well as their versatility in being used by themselves for "Oak Moss" fragrances.

Although the compound having the structure:

(and other tautomers) (shown as an equilibrium mixture) is known in the prior art (synthesis shown in J. Pharm. Soc., Japan, 59, 547 (1939) by J. Okazaki), nothing in the prior art suggests either implicitly or explicitly the use of such compounds or equilibrium mixture or constituents of said equilibrium mixture in the fields of perfumery and in tobacco aromatization.

BRIEF DESCRIPTION OF THE DRAWINGS

FIG. 3 is the nuclear magnetic resonance spectrum for the equilibrium mixture defined by the structures:

(and other tautomers) and named 2,4-dihydroxy-3,6-dimethylbenzonitrile prepared according to the process of Example II.

FIG. 4 is the Infrared spectrum for the equilibrium mixture defined by the structures:

(and other tautomers) and named 2,4-dihydroxy-3,6-dimethyl-benzontrile prepared according to the process of Example II.

THE INVENTION

Applicants have discovered that when one or more of the compounps:

3,6-dimethyl-2,4-dioxocyclohexanecarbonitrile;
2,4-dihydroxy-3,6-dimethylbenzonitrile; and
2,4-dihydroxy-3,6-dimethyl-1-acetophenone are combined with other perfume compositions they serve as substitute(s) for "Oak Moss" in the combination of components which determine the odor note of various perfume compositions.

In addition, each of these chemicals, taken alone or together, not only simulates with great fidelity the characteristic odor note of "Oak Moss", but each of them, taken alone or in combination, are less expensive than natural "Oak Moss" or its prior art synthetic simulations. Each of the compounds is prepared from readily available materials in commercial syntheses. The discovery of the unexpected, unobvious and advantageous aroma nuances imparted by each of these chemicals, taken alone or in combination, when combined with other perfume components becomes more significant since its value in perfumy cannot be predicted from the knowledge of other nitriles, or other acetylcycloalkene derivatives.

It has also been discovered that novel solid and liquid tobacco flavoring compositions, as well as novel tobacco compositions, having sweet, smokey, woody and "Oak Moss"-like aromas prior to smoking and in the mainstream and in the side-stream on smoking, and tobacco articles containing same may be provided by one or more of the substituted dimethyl dihydroxy benzene and cyclohexadiene compounds of our invention.

The substituted dimethyl dihydroxy benzene and cyclohexadiene compounds of our invention may be defined as an equilibrium mixture having the generic structure:

wherein the dashed line represents a carbon-carbon single bond or a carbon-carbon double bond and $R_1$ is selected from the group consisting of acetyl having the structure:

or nitrile having the structure:

When the dashed line is a carbon-carbon single bond, however, $R_1$ is only nitrile.

Applicants have also discovered that a sub-genus of the foregoing genus represents novel compounds and compositions of matter. This sub-genus is defined by the equilibrium mixture configuration:

wherein the dashed line represents a carbon-carbon single bond or a carbon-carbon double bond.

The substituted dimethyl dihydroxy benzene and cyclohexadiene compounds useful as indicated supra, may be produced preferably by one of the following processes.

A first process for producing the equilibrium mixture having the structure:

comprises first reacting an alkyl ester of cyano acetic acid having the structure:

with 2-hexen-4-one having the structure:

preferably in the presence of an alkali metal alkoxide such as sodium methoxide, thereby forming the first compound of our invention, 3,6-dimethyl-2,4-dioxocyclohexanecarbonitrile having the structure:

The reaction sequence is set forth as follows in an illustrative manner wherein the methyl ester of cyano acetic acid is used and wherein the alkali metal alkoxide used is sodium methoxide:

The resulting equilibrium mixture including the material having the structure:

may then, if desired, be reacted with an aromatizing agent such as chlorine, bromine, hypochlorous acid, NOCl, or an N-halosuccinimide thereby forming the completely aromatized equilibrium mixture containing 2,4-dihydroxy-3,6-dimethyl-benzonitrile having the structure:

according to the reaction:

In reaction (i) involving the reaction of an alkyl ester of cyano acetic acid and 4-hexen-2-one, it is preferable that the reaction temperature be in the range of from about 60° C up to about 120° C; and it is also preferable that the reaction take place in an inert solvent such as anhydrous methanol. The mole ratio of alkali metal alkoxide:4-hexen-2-one is preferably about 1:1, although either material can be used in excess. At the end of the reaction the resulting equilbrium mixture which includes 3,6-dimethyl-2,4-dioxocyclohexanecarbonitrile, is crystallized out as a precipitate and may be recrystallized using aqueous methanol thereby affording an essentially "pure" colorless product.

The reaction (ii) illustrated as follows:

preferably takes place by first dissolving the equilibrium mixture containing 3,6-dimethyl-2,4-dioxocyclohexanecarbonitrile in an inert solvent such as glacial acetic acid. The resulting solution is then cooled to a temperature in the range of 0°–20° C, whereupon either chlorine is sparged through the reaction mass or the reaction mass is intimately admixed with N-chlorosuccinimide or bromine or N-bromosuccinimide or nitrosyl chloride or hypochlorous acid. It is preferable that the reaction mass be maintained at a temperature in the range of 40°–80° C for a period of time of from 1 up to 5 hours, in order to insure the reaction's completion. At the end of this reaction, the product having the structure:

is extracted using an extractant such as toluene and then crystallized from a medium such as aqueous methyl alcohol.

One aspect of our invention provides an organoleptically improved smoking tobacco product and additives therefor, as well as methods for making same whereby specific desired sweet, smokey, woody and "Oak Moss" flavor characteristics (prior to smoking and on smoking; in the mainstream and in the sidestream) are created or enhanced or modified or augmented and may be readily controlled and maintained at the desired uniform level regardless of variations in the tobacco components of the blend.

This invention further provides improved tobacco additives which are used to augment or enhance various desirable tobacco flavoring characteristics, e.g., sweet, smokey, woody and "Oak-Moss"-like flavoring notes.

In carrying out this aspect of our invention, we add to smoking tobacco materials or a suitable substitute therefor (e.g. dried lettuce leaves) an aroma and flavor additive containing as an active ingredient one or more of the substituted dimethyl dihydroxy benzene and cyclohexadiene compounds of our invention; (i) 3,6-dimethyl-2,4-dioxocyclohexanecarbonitrile; (ii) 2,4-dihydroxy-3,6-dimethylbenzonitrile; and (iii) 2,4-dihydroxy-3,6-dimethyl-1-acetophenone.

In addition to the substituted dimethyl dihydroxy benzene and cyclohexadiene compounds of our invention, other flavoring and aroma additives may be added to the smoking tobacco material or substitute therefor, either separately or in admixture with the substituted dimethyl dihydroxy benzene and cyclohexadiene compounds as follows:

I. Synthetic Materials

Beta-ethyl-cinnamaldehyde;
Eugenol;
Dipentene;
Damascenone;
Maltol;
Ethyl Maltol;
Delta undecalactone;
Delta decalactone;
Benzaldehyde;
Amyl Acetate;
Ethyl Butyrate;
Ethyl Valerate;
Ethyl Acetate;
2-Hexanol-1;
2-Methyl-5-isopropyl-1,3-nonadiene-8-one;
2,6-Dimethyl-2,6-undecadiene-10-one;
2-Methyl-5-isopropyl acetopheneone;
2-Hydroxy-2,5,5,8a-tetramethyl-1-(2-hydroxyethyl)-decahydronaphthalene;
Dodecahydro-3a,6,6,9a-tetramethyl naphtho-(2,1b)-furan;
4-Hydroxy hexanoic acid, gamma lactone; and
Polyisoprenoid hydrocarbons defined in Example V of U.S. Pat. No. 3,589,372, issued on June 29, 1971.

II. Natural Oils

Celery seed Oil;
Coffee extract;
Bergamot Oil;
Cocoa extract;
Nutmeg Oil; and
Origanum Oil.

An aroma and flavoring concentrate containing one or more substituted dimethyl dihydroxy benzene and cyclohexadiene compounds of our invention and if desired, one or more of the above-indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g. lettuce leaves) or mixtures thereof. The proportions of flavoring additives may be varied in accordance with taste but insofar as enhancement or the imparting of natural and/or sweet and/or "Oak Moss" notes, we have found that satisfactory results are obtained if the proportion by weight of the sum total of substituted dimethyl dihydroxy benzene and cyclohexadiene compounds of our invention to smoking tobacco material is between 250 ppm and 1,500 ppm (0.025%-0.15%) of the active ingredients to the smoking material. We have further found that satisfactory results are obtained if the proportion by weight of the sum total of substituted dimethyl dihydroxy benzene and cyclohexadiene compounds used to flavoring material is between 2,500 and 15,000 ppm (0.25%-1.5%).

Any convenient method for incorporating the substituted dimethyl dihydroxy benzene and cyclohexadiene compounds of our invention into the tobacco product may be employed. Thus, the substituted dimethyl dihydroxy benzene and cyclohexadiene compounds of our invention taken alone or along with other flavoring additives may be dissolved in a suitable solvent such as ethanol, diethyl ether or any other volatile non-reactive and compatible organic solvents and the resulting solution may either be sprayed on the cured, cased and blended tobacco material or the tobacco material may be dipped into such solution. Under certain circumstances, a solution of the substituted dimethyl dihydroxy benzene and cyclohexadiene compounds of our invention taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

In accordance with one specific example of our invention, an aged, cured and shredded domestic burley tobacco is sprayed with a 20% ethyl alcohol solution of 2,4-dihydroxy-3,6-dimethylacetophenone in an amount to provide a tobacco composition containing 800 ppm by weight of 2,4-dihydroxy-3,6-dimethylacetophenone on a dry basis. Thereafter, the alcohol is removed by evaporatiion and the tobacco is manufactured into cigarettes by the usual techniques. The cigarette when treated as described has a desired and pleasing aroma which is detectable in the main and side streams when the cigarette is smoked. This aroma is described as being sweet, smokey, woody and "Oak Moss"-like.

While our invention is particularly useful in the manufacture of smoking tobacco, such as cigarette tobacco, cigar tobacco and pipe tobacco, other tobacco products formed from the sheeted tobacco dust or fines may also be used. Likewise, the substituted dimethyl dihydroxy benzene and cyclohexadiene compounds of our invention can be incorporated with materials such as filter tip materials, seam paste, packaging materials and the like which are used along with tobacco to form a product adapted for smoking. Furthermore, the substituted dimethyl dihydroxy benzene cyclohexadiene compounds of our invention can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials, or both.

The substituted dimethyl dihydroxy benzene and cyclohexadiene compounds of our invention and one or more auxiliary perfume ingredients, including, for example, alcohols, aldehydes, other nitriles, other ketones, esters, cyclic esters (lactones), natural essential oils and synthetic essential oils may be admixed so that the combined odors of the individual components product a pleasant and desired fragrance, particularly and preferably in "Mousse de Chene" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporatiion and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more of the substituted dimethyl dihydroxy benzene and cyclohexadiene compounds of our invention can be used to alter, modify or enhance the aroma characteristics of a perfume composition, for example, by utilizing or moderating the olfactory reaction contributed by another ingredient in the composition.

The amount of substituted dimethyl dihydroxy benzene and cyclohexadiene compounds of our invention which will be effective in perfume compositions as well as in prefumed articles and colognes depends on many factors, including the other ingredients, their amounts and the effects which are desired. It has been found that perfume compositions containing as little as 0.01% of substituted dimethyl dihydroxy benzene and cyclohexadiene compounds of our invention or even less (e.g., 0.005%) can be used to impart or augment or enhance "Oak Moss"-like nuances to soaps, cosmetics or other products. The amount employed can range up to 70% of the fragrance components and will depend on considerations of cost, nature of the end product, the effect desired on the finished product and the particular fragrance sought.

The substituted dimethyl dihydroxy benzene and cyclohexadiene compounds of our invention are useful [taken alone or together with other ingredients in perfume compositions] as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of substituted dimethyl dihydroxy benzene and cyclohexadiene compounds of our invention will suffice to impart an intense "Oak Moss" note to "Mousse de Chene" or to Crepe de Chene perfumery formulations. Generally, no more than 3% of substituted dimethyl dihydroxy benzene and cyclohexadiene compounds of our invention based on the ultimate end product, is required in the perfume composition.

In addition, the perfume composition or fragrance composition of our invention can contain a vehicle, or carrier for the substituted dimethyl dihydroxy benzene cyclohexadiene compounds of our invention. The vehicle can be a liquid such as non-toxic alcohol, a non-toxic glycol, or the like. The carrier can also be an absorbent solid, such as a gum e.g., gum arabic or components for encapsulating the composition (such as gelatin).

It will thus be apparent that the substituted dimethyl dihydroxy benzene and cyclohexadiene compounds of our invention can be utilized to alter, modify or enhance sensory properties, particularly organoleptic properties, such as flavor(s) and/or fragrance(s) of a wide variety of consumable materials.

The following examples serve to illustrate processes for producing the substituted dimethyl dihydroxy benzene and cyclohexadiene compounds of our invention and also serve to illustrate the usefulness of the substituted dimethyl dihydroxy benzene and cyclohexadiene compounds of our invention for augmenting, enhancing and imparting aroma and taste characteristics to perfumes, perfumed articles, tobaccos and tobacco flavors.

It will be understood that these examples are illustrative and the invention is to be considered restricted thereto only as indicated in the appended claims.

All parts and percentages given herein are by weight unless otherwise specified.

EXAMPLE I

PREPARATION OF 3,6-DIMETHYL-2,4-DIOXOCYCLOHEXANECARBONITRILE

Reaction:

To a solution of sodium methoxide (162 grams, 3 moles) in 400 mls of anhydrous methanol is added, dropwise, 276 grams (3.2 moles) of methylcyanoacetate over a period of 1 hour at 60° C with stirring. The resulting slurry is stirred at 60° C for 10 minutes, whereupon 288 grams (3.0 moles) of 2-hexen4-one is added over a 20 minute period. The resulting reaction mixture is stirred and heated at reflux for 6 hours, whereupon a distillation take-off condenser is affixed to the reaction flask and 240 mls of methanol are removed under reduced pressure (65 mm Hg). The reaction mixture is then cooled to room temperature and poured into 2 liters of water. Toluene (500 ml) is added and the mixture is transferred to a separatory funnel. The aqueous layer is removed and again extracted with toluene (500 mls). To the aqueous solution, 500 mls of 18% HCl are added with external cooling at 25° C, whereupon a solid material precipitates. The solid is filtered, dried and recrystallized from aqueous methanol to afford colorless needles of 3,6-dimethyl-2,4-dioxocyclohexanecarbonitrile (338 grams, 68.3% yield based on 2-hexen-4-one); m.p. 178°–179° C. The resulting product is represented by the following equilibrium mixture:

The NMR analysis is as folows:

| δ, ppm | Interpretation |
|---|---|
| 1.26 (3H, d, J=7Hz) | Methyl group A |
| 1.64 (3H, s) | Methyl group B |
| 4.84 (2H, s) | Hydroxyl groups |

Figure 1:
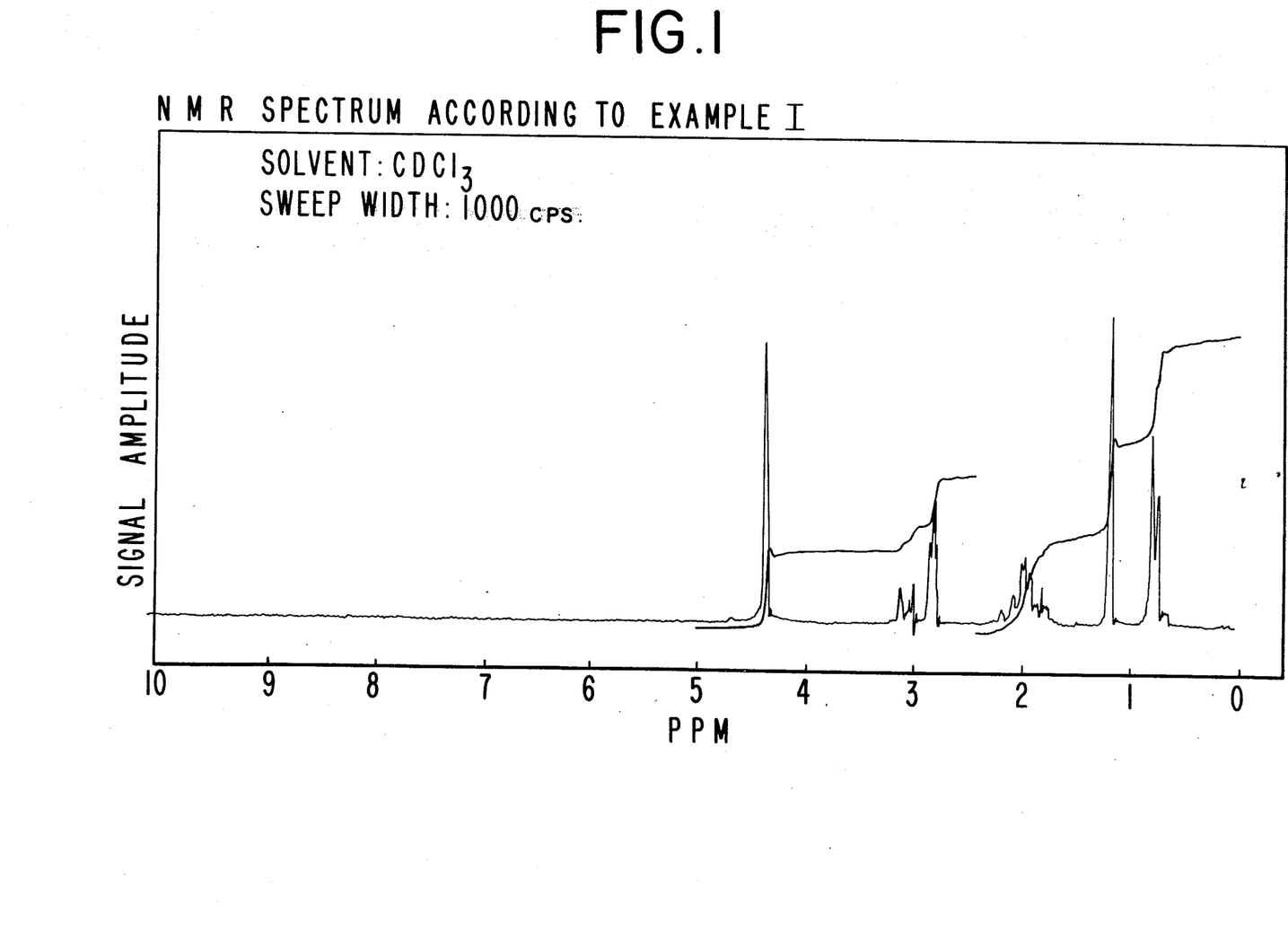
FIG. 1 is the nuclear magnetic resonance spectrum for the compound 3,6-dimethyl-2,4-dioxocyclohexanecarbonitrile produced according to the process of Example I.
Figure 2:
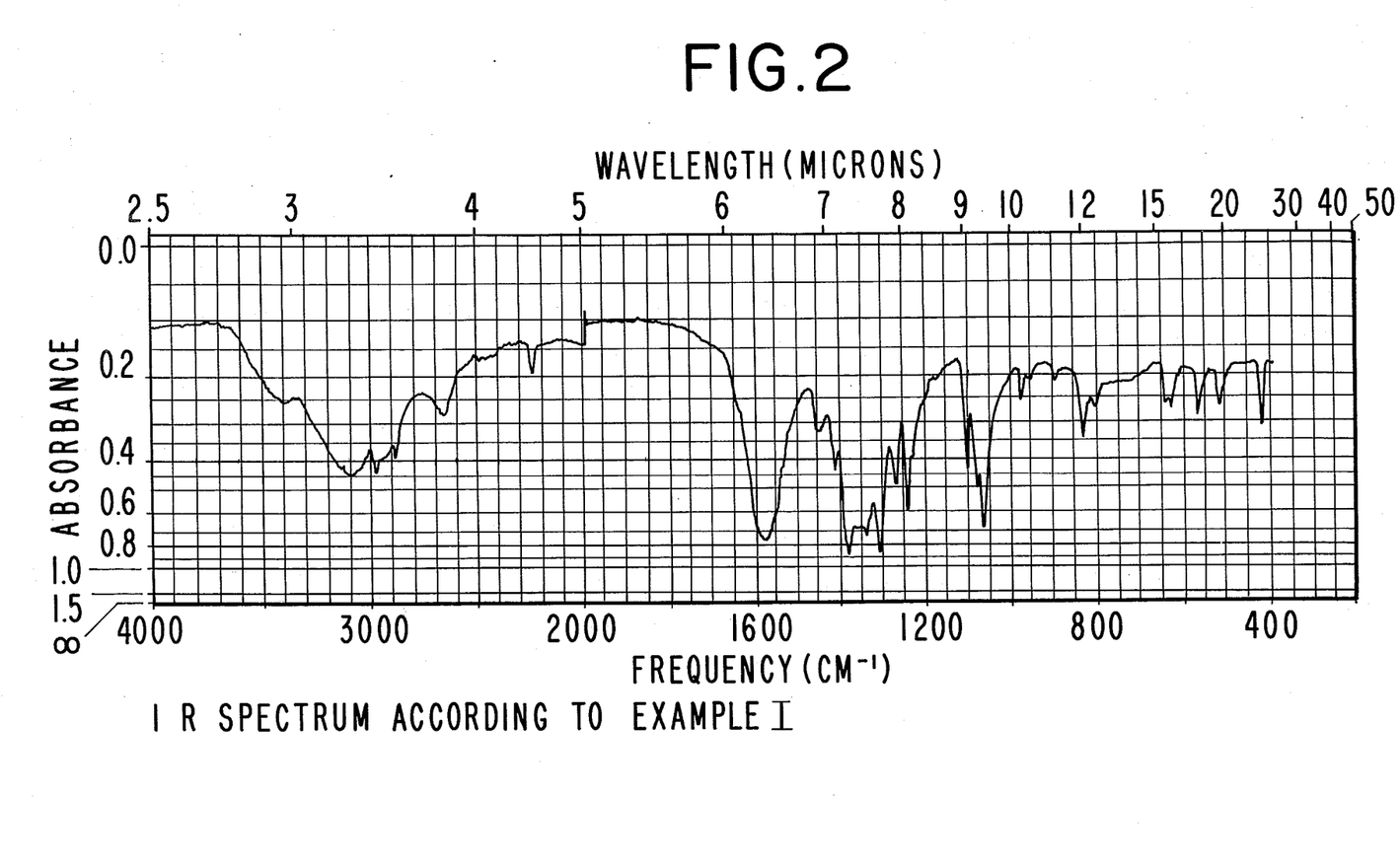
FIG. 2 is the Infrared spectrum for the compound 3,6-dimethyl-2,4-dioxocyclohexanecarbonitrile produced according to the process of Example I.

The Infrared analysis is as follows:
O–H stretch 3100 $cm^{-1}$ and 3400 $cm^{-1}$;
C≡N stretch 2240 $cm^{-1}$;
C═O stretch 1580 $cm^{-1}$.
The Mass Spectral analysis is as follows:
m/e= 98, 69, 165, 81, 70, 42.
The NMR spectrum is set forth in FIG. 1. The Infrared spectrum is set forth in FIG. 2.

EXAMPLE II

PREPARATION OF 2,4-DIHYDROXY-3,6-DIMETHYLBENZONITRILE

Reaction:

3,6-Dimethyl-2,4-dioxocyclohexanecarbonitrile (165 grams, prepared according to Example I) is dissolved in 300 mls of glacial acetic acid. The resulting solution is cooled to 5° C, whereupon 64 grams of chlorine is bubbled through the reaction mass using a gas dispersion tube. The reaction mixture is heated at 50° C for 1 hour subsequent to the chlorine addition and 3 liters of water are added thereto. The resulting aqueous solution is extracted three times with 250 mls of toluene (the toluene extracts are discarded) and evaporated under reduced pressure to afford a final volume of 800 mls. Upon standing, 95 grams of crystals are recovered in two crops. Recrystallization from aqueous methanol yields light-tan needles, m.p. 162°–163° C, consisting of 60% 2,4-dihydroxy-3,6-dimethylbenzonitrile and 40% 3,6-dimethyl-2,4-dioxocyclohexanecarbonitrile (% composition determined by NMR).

NMR, IR and Mass Spectral analyses confirm the structure:

The NMR analysis is as follows:

| δ, ppm | Interpretation |
|---|---|
| 2.0 (3H, s) | Methyl groups |
| 2.3 (3H, s) | |
| 4.78 (2H, broad s) | Hydroxyl groups |
| 6.3 (1H, s) | $H_A$ |

Figure 3:
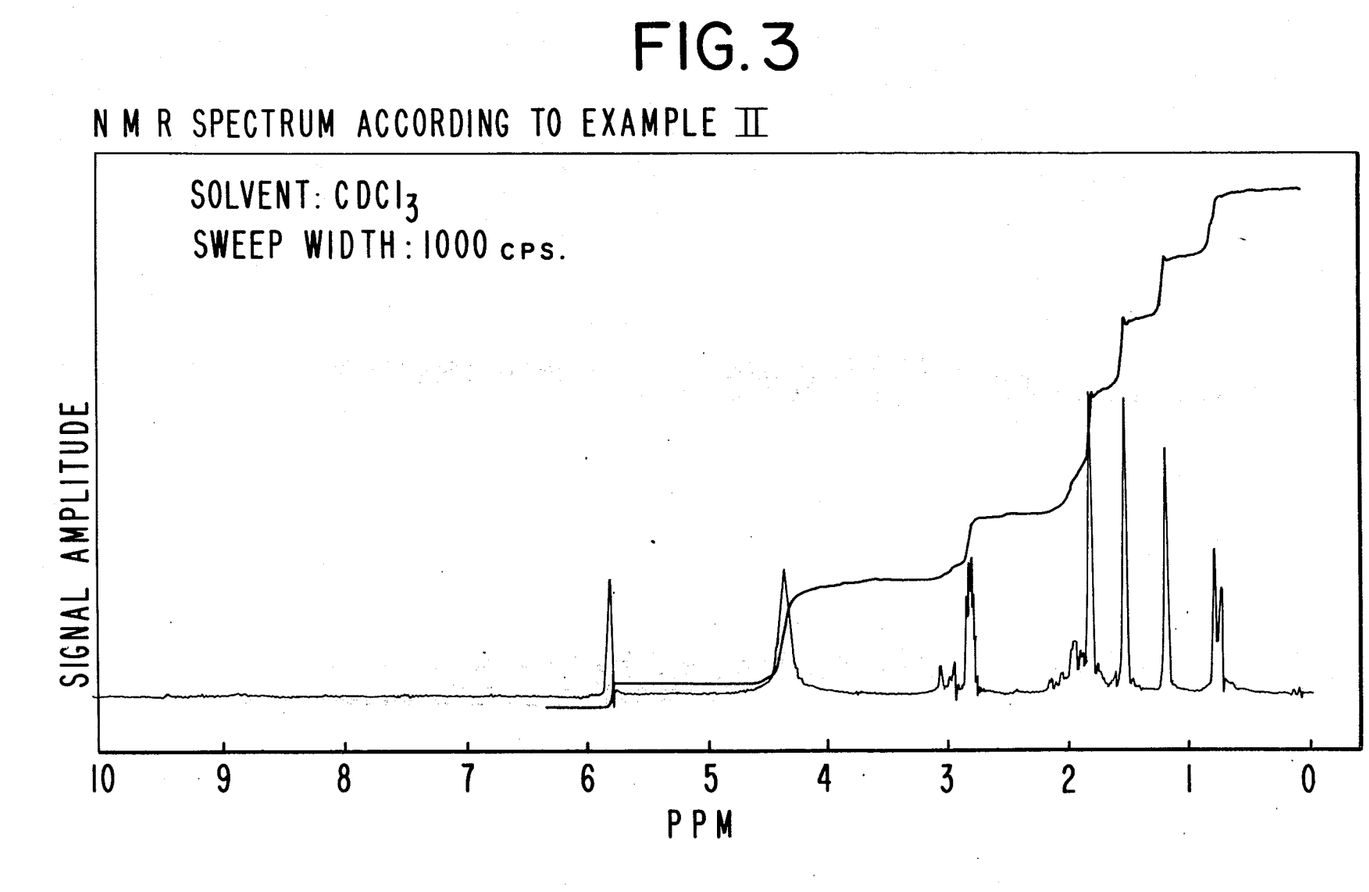
Figure 4:
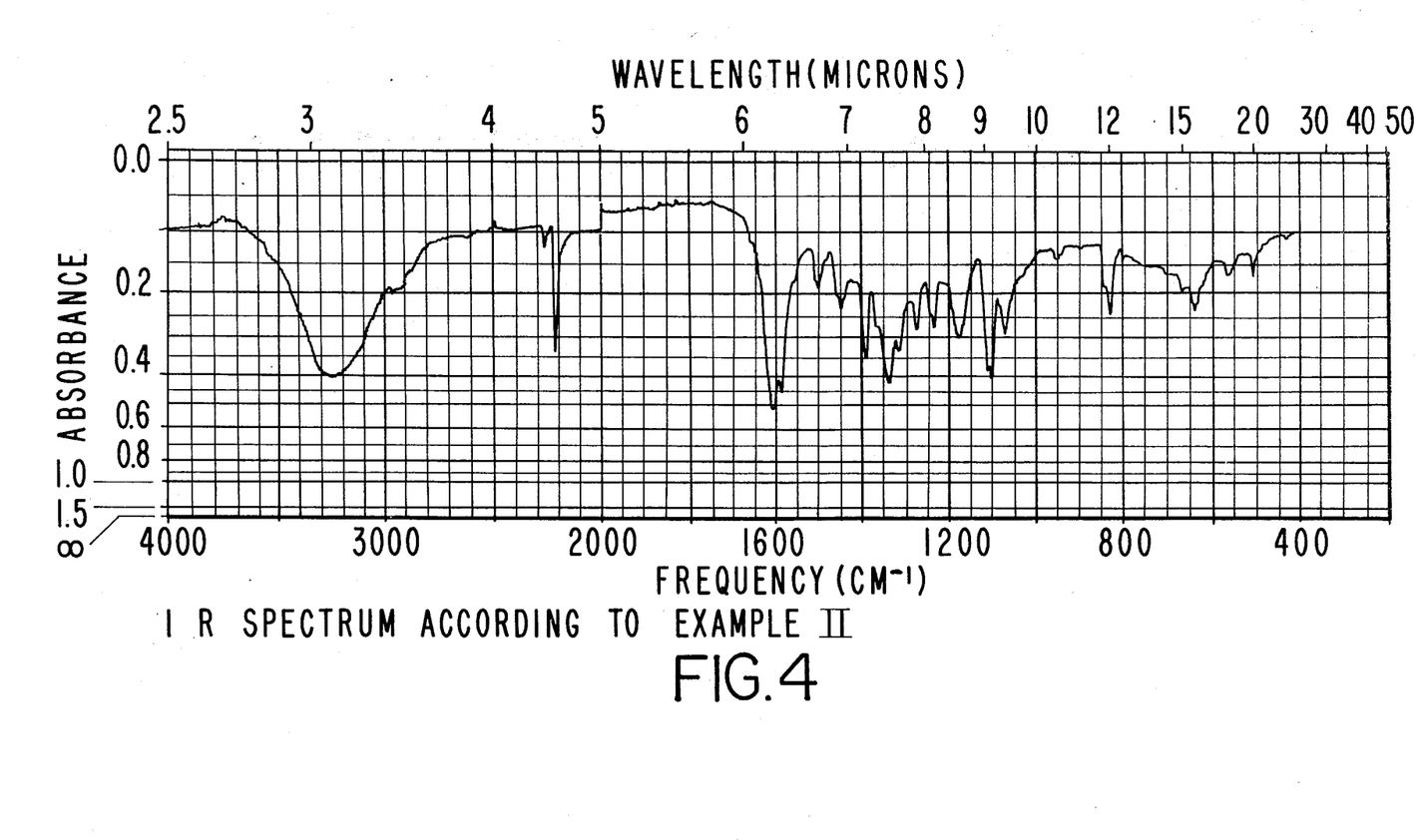

The Infrared analysis is as follows:
3260 $cm^{-1}$ (broad) O–H stretch
2220 $cm^{-1}$ C≡N stretch
The Mass Spectral analysis is as follows:
m/e=163, 69, 98, 39, 27, 162.
The NMR spectrum is set forth in FIG. 3. The Infrared spectrum is set forth in FIG. 4.

EXAMPLE III

PREPARATION OF 2,4-DIHYDROXY-3,6-DIMETHYLACETOPHENONE

Reaction:

Reaction:

Into a 12 liter reaction flask equipped with stirrer, thermometer and reflux condenser are added 300 grams of potassium hydroxide dissolved in 3 liters of methanol. To the methanol/potassium hydroxide mixture is added 3 moles (588 grams) of 2,4-dihydroxy-3,6-dimethyl-carbomethoxybenzene ("Veramoss"). The reaction mixture is heated to 68° C and refluxing is commenced. At this point, an additional amount of KOH solution is added over a period of 45 minutes while maintaining the reaction temperature at 68°–75° C. The reaction mass continues to be heated and refluxed for a period of 4 hours, at the end of which time 3600 ml of 12% hydrochloric acid solution is added over a period of 30 minutes. At the end of the addition of the hydrochloric acid the methanol is removed and the reaction mass is allowed to cool down, yielding crystals of β-Orcenol having the structure:

The resulting β-Orcenol (20 grams/0.143 moles) is then placed in a 250 ml reaction flask equipped with gas inlet tube and gas outlet tube and cooling bath. Acetonitrile (0.28 moles/12 grams), zinc chloride (4 grams) and anhydrous diethyl ether (100 ml) are added to the reaction mass and hydrogen chloride gas is passed through the reaction mass for a period of 2 hours at a temperature of 0° C. At the end of the 2 hour period, the hydrogen chloride gas addition is complete and the reaction mass is permitted to warm up to room temperature with stirring. 22 Grams of crystals are filtered. The resulting product has the structure:

The resulting material is then dissolved in 100 ml water in a 250 flask equipped with stirrer and reflux condenser. The reaction mass is heated to mild reflux for a period of 1.2 hours and then cooled to room temperature. The resulting crystals are filtered. NMR, IR and Mass Spectral analyses yield the information that the structure of the resulting material is:

The foregoing reaction sequence is also described in J. Pharm. Soc. Japan, 59, 547 (1939) in an article by J. Okazaki.

The resulting material is actually an equilibrium mixture as shown by the following equilibrium:

(and other tautomers).

(and other tautomers).

EXAMPLE IV

TOBACCO FORMULATION

A tobacco mixture is produced by admixing the following ingredients:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of 2,4-dihydroxy-3,6-dimethyl acetophenone prepared according to Example IV. The control cigarettes not containing the 2,4-dihydroxy-3,6-dimethyl acetophenone prepared according to the process of Example IV and the experimental cigarettes which contain the 2,4-dihydroxy-3,6-dimethyl acetophenone are evaluated by paired comparison and the results are as follows:

The experimental cigarettes are found to have a sweet, slightly smokey, slightly woody, oakmoss-like aroma prior to smoking and a woody, oakmoss-like aroma on smoking in both the mainstream and in the sidestream.

The tobacco of the experimental cigarettes, compared with the control cigarettes, is more aromatic and more tobacco-like. In addition, the control cigarettes have none of the interesting and pleasant oakmoss aroma in the mainstream or in the sidestream on smoking.

EXAMPLE V

CHYPRE PERFUME COMPOSITIONS

The following example illustrates the use in perfumery compositions of 2,4-dihydroxy-3,6-dimethyl acetophenone produced according to Example IV. This material can replace partially or completely natural "Oak Moss". By adding any quantity of the 2,4-dihydroxy-3,6-dimethyl acetophenone, the odor quality of natural "Oak Moss" may be achieved with great fidelity but with great reduction in cost:

| Ingredient | Parts by Weight |
|---|---|
| Oak Moss Extract (Evernia) | 2.5 |
| 2,4-Dihydroxy-3,6-dimethyl acetophenone produced according to Example IV | 2.5 |
| Oil of Bergamot | 22.5 |
| Oil Vetiver Bourbon | 7.5 |
| Oil of Lavender | 5.0 |
| Oil Sandalwood | 7.0 |
| Oil Patchouli | 1.0 |
| Oil of Cloves | 3.5 |
| Extract of Jasmine | 10.0 |
| Oil of Rose | 8.0 |
| Isobutyl Salicylate | 7.0 |
| Cinnamyl Alcohol | 5.0 |
| Heliotropin | 10.0 |
| Coumarin | 5.0 |
| Oleoresin Tonka Beans | 2.0 |
| Methyl Nonyl Acetaldehyde | 1.5 |
| | 100.0 |

EXAMPLE VI

CHYPRE PERFUME COMPOSITIONS

The following example illustrates the use in perfumery compositions of 2,4-dihydroxy-3,6-dimethyl acetophenone produced according to Example IV. This material can replace partially or completely natural "Oak Moss". By adding any quantity of the 2,4-dihydroxy-3,6-dimethyl acetophenone, the odor quality of natural "Oak Moss" may be achieved with great fidelity but with great reduction in cost:

| Ingredient | Parts by Weight |
|---|---|
| Oil of Sandalwood | 29.6 |
| Phenyl Ethyl Alcohol | 15.0 |
| Oil of Cedarwood | 5.0 |
| Oil Lavender | 10.0 |
| Oil Patchouli | 30.0 |
| Oil Vetiver | 3.0 |
| Extract of Tonka Beans | 2.0 |
| 2,4-Dihydroxy-3,6-dimethyl acetophenone produced according to Example IV | 1.5 |
| Oil Ylang Ylang | 0.5 |
| Oil Sassafras | 0.3 |
| Dimethyl Hydroquinone | 0.2 |
| Oleoresin Labdanum | 0.1 |
| Castoreum Extract (3% solution) | 1.0 |
| Vanillin | 0.4 |
| Heliotropin | 0.7 |
| Musk Ambrette | 0.7 |
| | 100.0 |

EXAMPLE VII

CHYPRE PERFUME COMPOSITIONS

The following example illustrates the use in perfumery compositions of 2,4-dihydroxy-3,6-dimethyl acetophenone produced according to Example IV. This material can replace partially or completely natural "Oak Moss". By adding any quantity of the 2,4-dihydroxy-3,6-dimethyl acetophenone, the odor quality of natural "Oak Moss" may be achieved with great fidelity but with great reduction in cost:

| Ingredient | Parts by Weight |
|---|---|
| Coumarin | 17.6 |
| Oil Sandalwood | 8.8 |
| 2,4-Dihydroxy-3,6-dimethyl acetophenone produced according to Example IV | 8.8 |
| Oil Patchouli | 8.8 |
| Oil Vetiver | 5.9 |
| Linalyl Acetate | 35.4 |
| Phenylethyl Alcohol | 14.7 |
| | 100.0 |

EXAMPLE VIII

CHYPRE PERFUME COMPOSITIONS

The following example illustrates the use in perfumery compositions of 2,4-dihydroxy-3,6-dimethyl acetophenone produced according to Example IV. This material can replace partially or completely natural "Oak Moss". By adding any quantity of the 2,4-dihydroxy-3,6-dimethyl acetophenone, the odor quality of natural "Oak Moss" may be achieved with great fidelity but with great reduction in cost:

| Ingredient | Parts by Weight |
|---|---|
| Linalyl Acetate | 32.8 |
| Coumarin | 8.2 |
| Oleoresin Tonka Beans | 4.9 |
| Oak Moss Extract (Evernia) | 6.1 |
| 2,4-Dihydroxy-3,6-dimethyl acetophenone produced according to Example IV | 4.1 |
| Oil Patchouli | 4.9 |
| Oil Cedarwood | 24.6 |
| Oil Sandalwood | 8.2 |
| Oil Vetiver Reunion | 4.1 |
| Vanillin | 2.1 |
| | 100.0 |

EXAMPLE IX

CHYPRE PERFUME COMPOSITIONS

The following example illustrates the use in perfumery compositions of 2,4-dihydroxy-3,6-dimethyl acetophenone produced according to Example IV. This material can replace partially or completely natural "Oak Moss". By adding any quantity of the 2,4-dihydroxy-3,6-dimethyl acetophenone, the odor quality of natural "Oak Moss" may be achieved with great fidelity but with great reduction in cost:

| Ingredient | Parts by Weight |
|---|---|
| Oak Moss Extract (Evernia) | 2.0 |

-continued

| Ingredient | Parts by Weight |
|---|---|
| 2,4-Dihydroxy-3,6-dimethyl acetophenone produced according to Example IV | 15.0 |
| Oil of Bergamot | 13.0 |
| Oil Vetiver Bourbon | 7.5 |
| Oil of Lavender | 5.0 |
| Oil Sandalwood | 7.0 |
| Oil Patchouli | 1.0 |
| Oil of Cloves | 3.5 |
| Extract of Jasmine | 8.0 |
| Oil of Rose | 4.0 |
| Phenyl Ethyl Alcohol | 4.0 |
| Isobutyl Salicylate | 7.0 |
| Cinnamyl Alcohol | 5.0 |
| Heliotropin | 9.5 |
| Coumarin | 5.0 |
| Oleoresin Tonka Beans | 2.0 |
| Methyl Nonyl Acetaldehyde | 1.5 |
| | 100.0 |

EXAMPLE X

CHYPRE PERFUME COMPOSITIONS

The following example illustrates the use in perfumery compositions of 2,4-dihydroxy-3,6-dimethyl acetophenone produced according to Example IV. This material can replace partially or completely natural "Oak Moss". By adding any quantity of the 2,4-dihydroxy-3,6-dimethyl acetophenone, the odor quality of natural "Oak Moss" may be achieved with great fidelity but with great reduction in cost:

| Ingredient | Parts by Weight |
|---|---|
| Oil of Sandalwood | 3.0 |
| Oil of Rose | 1.0 |
| Oil of Cedarwood | 0.5 |
| Oil Lavender | 1.0 |
| Oil Patchouli | 2.0 |
| Oil Vetiver | 0.3 |
| Extract of Tonka Beans | 0.3 |
| 2,4-Dihydroxy-3,6-dimethyl acetophenone produced according to Example IV | 0.1 |
| 10% Solution Oil Ylang Ylang in Benzyl Benzoate | 5.0 |
| 10% Solution Oil Sassafras in Benzyl Benzoate | 3.0 |
| 10% Solution Dimethyl Hydroquinone in Benzyl Benzoate | 2.0 |
| 10% Solution Oleoresin Labdanum in Benzyl Benzoate | 1.0 |
| Castoreum Extract (3% Solution) | 0.1 |
| 10% Solution Vanillin in Benzyl Benzoate | 0.4 |
| Heliotropin | 0.1 |
| Musk Ambrette | 0.1 |
| Benzyl Benzoate | 80.1 |
| | 100.0 |

EXAMPLE XI

FOUGERE PERFUME COMPOSITIONS

The following example illustrates the use in perfumery compositions of 2,4-dihydroxy-3,6-dimethyl acetophenone produced according to Example IV. This material can replace partially or completely natural "Oak Moss". By adding any quantity of the 2,4-dihydroxy-3,6-dimethyl acetophenone, the odor quality of natural "Oak Moss" may be achieved with great fidelity but with great reduction in cost:

| Ingredient | Parts by Weight |
|---|---|
| Oil Lavender | 11.0 |
| Oil Patchouli | 5.0 |
| Coumarin | 8.0 |
| Heliotropin | 1.5 |
| Musk Xylol | 1.0 |
| Musk Ambrette | 0.5 |
| Oil Geranium | 2.5 |
| Alpha-Terpineol | 20.0 |
| Oil Cedarwood | 7.5 |
| Oil Vetiver Reunion | 6.0 |
| Phenylethyl Alcohol | 12.5 |
| para-Methylacetophenone | 2.5 |
| Linalyl Acetate | 7.5 |
| Amyl Salicylate | 5.0 |
| Oak Moss Extract (Evernia) | 4.0 |
| 2,4-Dihydroxy-3,6-dimethyl acetophenone produced according to Example IV | 4.5 |
| Oleoresin Labdanum | 1.0 |
| | 100.0 |

EXAMPLE XII

FOUGERE PERFUME COMPOSITIONS

The following example illustrates the use in perfumery compositions of 2,4-dihydroxy-3,6-dimethyl acetophenone produced according to Example IV. This material can replace partially or completely natural "Oak Moss". By adding any quantity of the 2,4-dihydroxy-3,6-dimethyl acetophenone, the odor quality of natural "Oak Moss" may be achieved with great fidelity but with great reduction in cost:

| Ingredient | Parts by Weight |
|---|---|
| 2,4-Dihydroxy-3,6-dimethyl acetophenone produced according to Example IV | 4.0 |
| Amyl Salicylate | 3.2 |
| Coumarin | 16.0 |
| Oleoresin Tonka Beans | 4.0 |
| Phenylethyl Alcohol | 2.8 |
| Heliotropin | 4.0 |
| Vanillin | 1.6 |
| Oil Vetiver Java | 13.6 |
| Oil Patchouli | 4.8 |
| Oil Lavender | 24.0 |
| Linalyl Acetate | 16.0 |
| Oil Neroli Bigarade | 6.0 |
| | 100.0 |

EXAMPLE XIII

PREPARATION OF A COSMETIC-POWDER COMPOSITION

A cosmetic powder is prepared by mixing in a ball mill, 100 grams of talcum powder with 0.25 grams of 2,4-dihydroxy-3,6-dimethyl acetophenone prepared according to Example IV. It has an excellent "Mousse de Chene" aroma.

EXAMPLE XIV

PERFUMED LIQUID DETERGENT

Concentrated liquid detergents with mousse aromas are prepared containing 0.10%, 0.15% and 0.20% of one of the following compounds:
(i) 2,4-dihydroxy-3,6-dimethyl acetophenone (prepared according to Example III);
(ii) 3,6-dimethyl-2,4-dioxocyclohexanecarbonitrile (prepared according to Example I); and
(iii) 2,4-dihydroxy-3,6-dimethylbenzonitrile (prepared according to Example II).

They are prepared by adding and homogeneously mixing an appropriate quantity of each of the materials (i), (ii) and (iii) in the liquid detergent. The detergents all possess an intense "Mousse de Chene" fragrance, the intensity increasing with greater concentrations of substituted dimethyl dihydroxy cyclohexadiene or cyclohexatriene compound (i), (ii) or (iii).

EXAMPLE XV

PREPARATION OF A COLOGNE AND HANDKERCHIEF PERFUME 3,6-Dimethyl-2,4-dioxocyclohexanecarbonitrile prepared according to Example I or 2,4-dihydroxy-3,6-dimethylbenzonitrile prepared according to Example II or 2,4-dihydroxy-3,6-dimethyl-1-acetyl benzene prepared according to Example III are each separately incorporated into a cologne at a concentration of 2.0%, 2.5%, 3.0% and 3.5% in 85% aqueous ethanol; and into a handkerchief perfume at concentrations of 15%, 20%, 25%, 30%, 35% and 40% (in 95% aqueous ethanol) in each of the cases with each of the compounds prepared according to Examples I, II and III, a distinct and definite "Mousse de Chene" aroma is imparted to the cologne and to the handkerchief perfume, the intensity increasing with increasing concentrations of substituted dimethyl dihydroxy benzene or cyclohexadiene compound.

EXAMPLE XVI

PREPARAION OF "CREPE DE CHENE" PERFUME FORMULATION

The following mixture is prepared:

| Ingredient | Parts by Weight |
| --- | --- |
| Vanillin | 2.0 |
| Myrrh Coeur (50% in diethyl phthalate) | 6.0 |
| Olibanum coeur (50% in diethyl phthalate) | 8.0 |
| Coumarin | 20.0 |
| Galaxolide (50% in diethyl phthalate)-Galaxolide is a registered trademark of International Flavors & Fragrances Inc. (prepared according to the process of Example XVII of U.S. Patent 3,360,530, issued on December 26, 1967 (6-oxa-1,1,2,3,3,8-hexamethyl-2,3,5,6,7,8-hexahydro-1H-benz[f]-indene) | 60.0 |
| Tolu Balsam (50% in diethyl phthalate) | 5.0 |
| Styrax | 3.0 |
| Labdanum (50% in diethyl phthalate) | 1.0 |
| Lyral (Registered trademark of International Flavors & Fragrances Inc., identifying 4-(4-methyl-4-hydroxy)-$\Delta^3$-cyclohexenecarboxaldehyde) | 15.0 |
| Sandalwood East Indian | 10.0 |
| Vetiver Acetate | 5.0 |
| Vertofix Coeur (reaction product of thujopsene and acetic anhydride) | 10.0 |
| Rose Absolute | 60.0 |
| Jasmine Absolute | 45.0 |
| Gamma-methyl ionone coeur | 25.0 |
| Civet, tincture (10% in absolute ethyl alcohol) | 15.0 |
| Eugenol | 10.0 |
| Isoeugenol | 15.0 |
| Tincture of Castoreum (20% in absolute ethanol) | 5.0 |
| Styrallyl Acetate | 7.0 |
| Ylang Extra | 5.0 |
| Bergamot Oil | 30.0 |
| 3,6-dimethyl-2,4-dioxocyclohexanecarbonitrile (produced according to Example I) | 12.5 |
| 2,4-dihydroxy-3,6-dimethyl-benzonitrile (prepared according to Example II) | 12.5 |
| 2,4-dihydroxy-3,6-dimethyl acetophenone (prepared according to Example III) | 12.5 |
| Veramoss (2,4-dihydroxy-3,6-dimethyl-1-carbomethoxy-benzene) | 60.0 |

The combination of 3,6-dimethyl-2,4-dioxocylohexanecarbonitrile (prepared according to Example I), 2,4-dihydroxy-3,6-dimethylbenzonitrile (prepared according to Example II) and 2,4-dihydroxy-3,6-dimethyl acetophenone (prepared according to Example III) enhances and enriches the "Oak Moss" notes and dry-out effect of this "Crepe de Chene" formulation.

EXAMPLE XVII

PREPARATION OF SOAP COMPOSITION

One hundred grams of soap chips are mixed with one gram each of the following materials:
(i) 3,6-dimethyl-2,4-dioxocylohexanecarbonitrile (prepared according to the process of Example I);
(ii) 2,4-dihydroxy-3,6-dimethylbenzonitrile (prepared according to the process of Example II); and
(iii) 2,4-dihydroxy-3,6-dimethyl acetophenone (prepared according to the process of Example III)

until a substantially homogeneous composition is obtained. The perfumed soap composition manifests an excellent mossy, "Mousse de Chene" aroma.

EXAMPLE XVIII

PREPARATION OF A DETERGENT COMPOSITION

A total of 100 grams of a detergent powder is intimately admixed with 0.15 grams of each of the following materials:
(i) 3,6-dimethyl-2,4-dioxocylohexanecarbonitrile (prepared according to the process of Example I);
(ii) 2,4-dihydroxy-3,6-dimethylbenzonitrile (prepared according to the process of Example II);
(iii) 2,4-dihydroxy-3,6-dimethyl acetophenone (prepared according to the process of Example III); and
(iv) 2,4-dihydroxy-3,6-dimethyl-1-carbomethoxybenene ("Veramoss")

until a substantially homogeneous composition is obtained. The composition has an excellent mossy aroma with excellent "Oak Moss" notes.

EXAMPLE XIX

PREPARATION OF A SOAP COMPOSITION

100 Grams of soap chips are mixed with one gram of the "Crepe de Chene" perfume formulation prepared according to Example XVI until a substantially homogeneous composition is prepared. The soap composition manifests an excellent "Crepe de Chene" character with enriched "Oak Moss" notes and excellent dry-out effect.

EXAMPLE XX

PREPARATION OF A DETERGENT COMPOSITION

A total of 100 grams of detergent powder is mixed with 0.20 grams of the perfume composition of Example XVI until a substantially homogeneous composition is obtained. This composition has an excellent "Crepe de Chene" aroma with good "Oak Moss" notes and unexpected dry-out effect.

EXAMPLE XXI

PREPARATION OF A COLOGNE AND HANDKERCHIEF PERFUME

The composition ("Crepe de Chene") of Example XVI is incorporated into a cologne at concentrations of 2.0%, 2.5%, 3.0%, 3.5%, 4.0%, 4.5% and 5.0% in 85% aqueous ehtanol; and into a handkerchief perfume at concentrations of 15%, 20%, 25%, 30%, 35% and 40% (in 95% aqueous ethanol). The use of the following compounds:
  (i) 3,6-dimethyl-2,4-dioxocyclohexanecarbonitrile (prepared according to the process of Example I);
  (ii) 2,4-dihydroxy-3,6-dimethylbenzonitrile (prepared according to the process of Example II);
  (iii) 2,4-dihydroxy-3,6-dimethyl acetophenone (prepared according to the process of Example III); and
  (iv) 2,4-dihydroxy-3,5-dimethyl-1-carbomethoxybenzene ("Veramoss")

to afford a distinct and definite strong "Oak Moss" aroma which is enhanced by the compounds prepared according to Examples I, II and III and whose dry-out effect is advantageously and unexpectedly improved as a result of using the compounds of Examples I, II and III in admixture. In addition, when the compounds of Examples I, II and III are used separately, similar enhancement and dry-out effects are obtained with enrichment of the "Oak Moss" notes.

What is claimed is:

1. A nitrile compound having the structure:

* * * * *